United States Patent
Powell

[11] Patent Number: 6,066,497
[45] Date of Patent: May 23, 2000

[54] CELL CULTURE APPARATUS

[75] Inventor: Alexander Robert Powell, Southport, United Kingdom

[73] Assignee: Powell Biological Machines Limited, United Kingdom

[21] Appl. No.: 08/776,891

[22] PCT Filed: Aug. 2, 1995

[86] PCT No.: PCT/GB95/01833

§ 371 Date: Feb. 12, 1997

§ 102(e) Date: Feb. 12, 1997

[87] PCT Pub. No.: WO96/05285

PCT Pub. Date: Feb. 22, 1996

[30] Foreign Application Priority Data

Aug. 16, 1994 [GB] United Kingdom ............... 9416499
Jan. 28, 1995 [GB] United Kingdom ............... 9501702
May 23, 1995 [GB] United Kingdom ............... 9510335

[51] Int. Cl.$^7$ .................................................. C12M 1/24
[52] U.S. Cl. ................................. 435/298.2; 435/303.3; 435/809; 435/304.1; 435/286.5
[58] Field of Search .................... 435/286.5, 286.7, 435/290.3, 298.1, 298.2, 299.2, 303.3, 304.1, 809; 422/64, 102, 104; 366/208, 213, 214; 494/16–18, 32, 35, 42

[56] References Cited

U.S. PATENT DOCUMENTS

| | | |
|---|---|---|
| 3,540,700 | 11/1970 | Freedman et al. . |
| 3,724,747 | 4/1973 | Unger et al. ............................ 494/42 |
| 3,732,149 | 5/1973 | Santero .............................. 435/298.2 |
| 3,740,321 | 6/1973 | Pagano et al. . |
| 3,827,943 | 8/1974 | Mann ................................. 435/298.2 |
| 3,847,749 | 11/1974 | Smith et al. . |
| 3,875,000 | 4/1975 | Kaneda . |
| 4,373,029 | 2/1983 | Nees . |
| 4,650,766 | 3/1987 | Harm et al. . |
| 4,717,668 | 1/1988 | Keilman et al. . |
| 5,037,754 | 8/1991 | Tanaka et al. . |

FOREIGN PATENT DOCUMENTS

| | | | |
|---|---|---|---|
| 0 164 888 | 12/1985 | European Pat. Off. . | |
| 62-289176 | 12/1987 | Japan ................. | 435/303.3 |
| 499293 | 1/1976 | U.S.S.R. ............. | 435/298.2 |
| 644822 | 1/1979 | U.S.S.R. ............. | 435/298.2 |
| 1578187 | 7/1990 | U.S.S.R. ............. | 435/298.2 |
| 1731801 | 5/1992 | U.S.S.R. ............. | 435/298.2 |
| 91/05705 | 5/1991 | WIPO ................. | 435/286.2 |

Primary Examiner—William H. Beisner
Attorney, Agent, or Firm—Foley & Lardner

[57] ABSTRACT

A cell culture apparatus is disclosed. The cell culture apparatus includes a chassis or supporting frame. The cell culture apparatus also includes a rotor releasably housing a plurality of cell culture vessels/roller bottles, the rotor being mounted about a substantially horizontal axis or shaft supported by said frame, with means provided to facilitate rotation of the rotor at a controlled speed. The cell culture apparatus also includes a reversible multi-channel pump or pumps, mounted on and rotating with the rotor. The cell culture apparatus also includes a manifold with one or more sealable external connections and a plurality of connections communicating with the individual channels of the multi-channel pump or pumps, each of the cell culture vessels being equipped with a microporous air vent to atmosphere and a dip tube. The dip tube is fixed with respect to the cell culture vessel and positioned to permit extraction of fluid when the cell culture vessel is stopped in a specific orientation. The dip tube of each vessel is individually connected to one channel of said multi-channel pump or pumps. The arrangement of the parts is such that the assembly comprising the rotor, cell culture vessels, pump, manifold and the connections to the cell culture vessels are rotatable about the horizontal axis. The arrangement also allows fluid to be injected into or extracted from the roller bottles simultaneously via a single external connection, under the influence of the multi-channel pump or pumps.

7 Claims, 8 Drawing Sheets

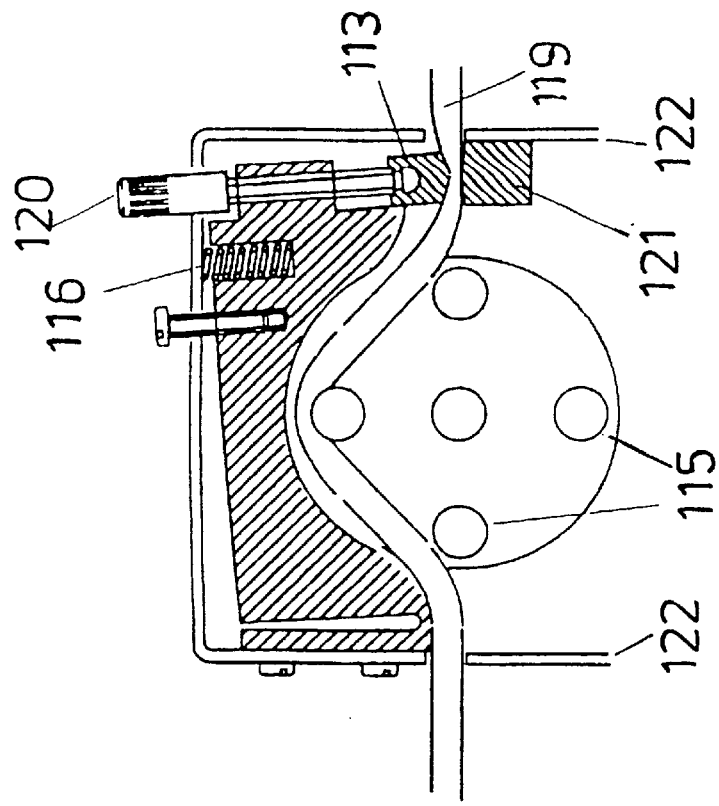
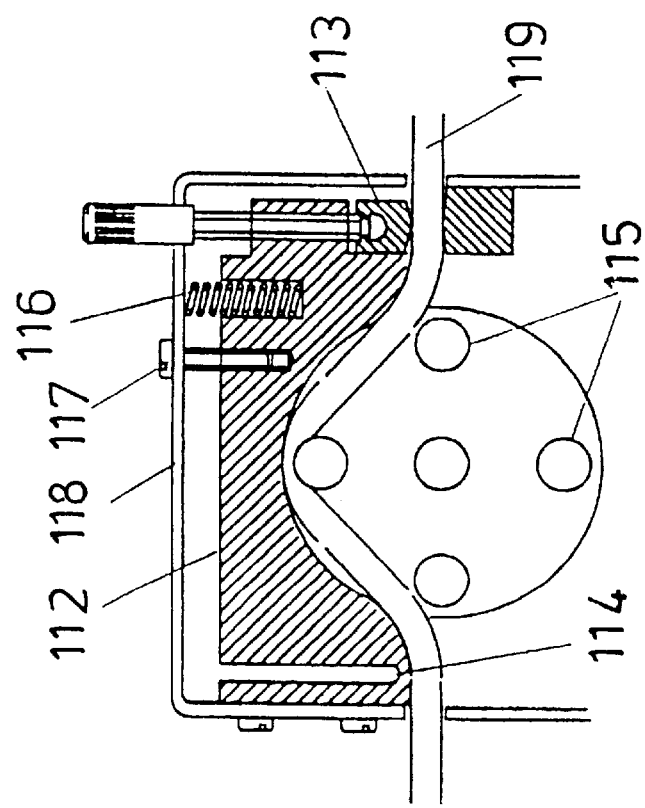

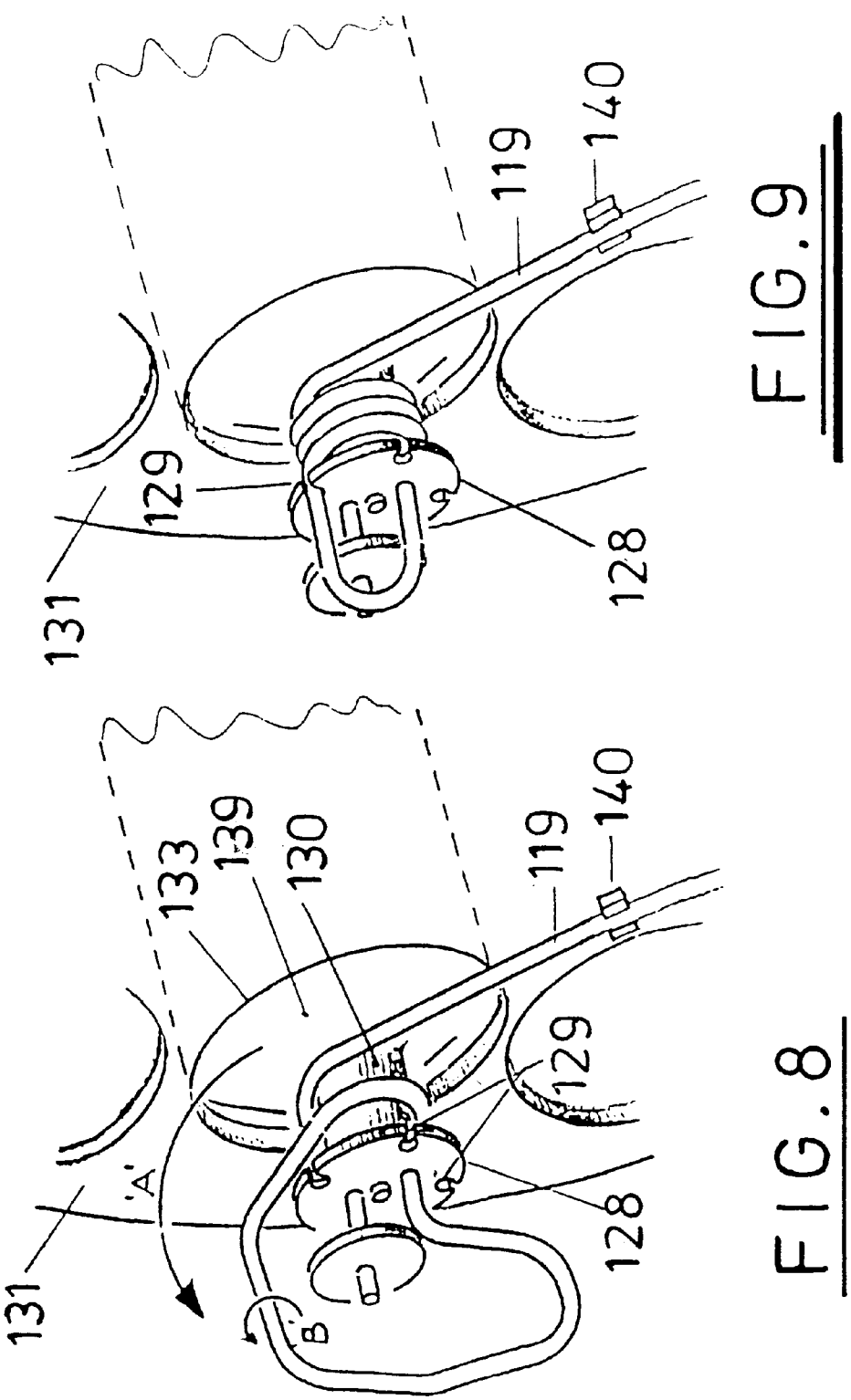

CELL CULTURE APPARATUS

TECHNICAL FIELD

This invention relates to apparatus for the large scale processing of cell cultures.

BACKGROUND TO THE INVENTION

The rapid growth of biotechnology has led to the need for large scale tissue culture techniques for anchorage dependent cells. Roller bottles are used extensively in the industry for this purpose. Cells are cultured whilst attached to the interior of the roller bottle. Existing roller bottle machines provide for rotation of the bottles to keep the cells bathed in culture medium during culture stages. The processing operations such as innoculation, culture medium supply, or harvesting for example which require the flow of fluids into or out of the roller bottle are carried out manually or by expensive mechanical handling systems such as robots.

For large scale production, this process can be awkward, time consuming, and carries the risk of infection of the bottle contents by foreign organisms during handling.

In some systems, the need to physically handle the roller bottles is eliminated by providing each bottle with a special cap that is equipped with a rotary seal and feed tubes that allows the bottle to rotate and yet facilitates the injection or extraction of process fluids. This system is prone to external infection via the rotary seals however, and is in any case mechanically complex and thus expensive.

A system that would provide aseptic access to the interior of a large number of roller bottles via a single connection whilst still allowing the bottles to rotate, but which did not require the use of a large number of rotating seals, would be of greater practical and economic advantage to large scale roller bottle processes using anchorage dependent cells.

DISCLOSURE OF INVENTION

According to one aspect of the present invention, there is provided, cell culture apparatus comprising a chassis or supporting frame, a rotor releasably housing a plurality of cell culture vessels/roller bottles, said rotor being mounted about a substantially horizontal axis or shaft supported by said frame, with means provided to facilitate rotation of the rotor at a controlled speed, a reversible multi-channel pump or pumps, mounted on and rotating with the rotor, a manifold with one or more sealable external connections and a plurality of connections communicating with the individual channels of the muti-channel pump or pumps, each of the cell culture vessels being equipped with a microporous air vent to atmosphere and a dip tube, the dip tube of each vessel being individually connected to one channel of said multi-channel pump or pumps, the arangement of the parts being such that the assembly comprising the rotor, cell culture vessels, pump, manifold and the connections to the cell culture vessels may be rotated about said horizontal axis, and the arrangement also allowing fluid to be injected into or extracted from the roller bottles simultaneously via a single external connection, under the influence of said multi-channel pump or pumps.

It is preferred to employ a multi-channel pump having a common pumping element, but as an alternative several pumps may be employed. It is convenient to use a pump of the peristaltic type.

Preferably means is provided for selectively opening and closing each of the connections individually whereby fluid is injected into or extracted from selected culture vessels.

The cell culture vessel may comprise a conventional roller bottle whose cap is replaced by a cap equipped with said microporous air vent and with said dip tube.

Alternatively, the cell culture vessel may be purpose made for the apparatus in which case it is proposed to dispense with the filling cap and to provide the vessel with an integral air vent and dip tube. These may be moulded or bonded in place. The use of an integral dip tube further reduces the cost and complexity, whilst the risk of external infections whilst connecting the bottle is likewise reduced.

Accordingly another aspect of the invention provides a cell culture vessel/roller bottle, comprising a substantially cylindrical culture vessel, a dip tube formed integrally in said vessel such that fluid may be fed into or withdrawn from the vessel via the said dip tube, and means formed integrally in said vessel to accommodate a microporous vent filter such that air may leave or enter the vessel in order to allow pressure equalisation with the atmosphere as fluid is fed into or withdrawn from from the vessel without allowing the entry of contaminating particles or organisms.

As an alternative to providing each vessel with a filter, one filter may be arranged so as to vent a number of vessels via a vent manifold and interconnecting tube system similar to that already described for the distribution of fluid to/from the vessels.

For certain processes that require the introduction of gasses such as carbon dioxide into the roller bottle to enhance cell growth, the vessel vent, (or vent manifold) may be equipped with a valve or closure to prevent loss of the gas to atmosphere by diffusion during culture stages, said valve or closure being temporarily opened to atmosphere to allow pressure equalisation whilst fluids are being pumped into or out of the vessel.

The cell culture vessel is primarily intended for use with the above-described cell culture apparatus. More particularly, the bottles may be connected to the pump tubes prior to sterilisation, thereby further reducing the risk of contamination whilst setting up the apparatus.

Accordingly, the present invention also provides an assembly comprising a plurality of cell culture vessels each having a dip tube by which fluid may be fed into or withdrawn from the vessel and a vent filter for equalising pressure within the vessel, and further comprising a fluid manifold having a sealable external connection, and a respective connection between the manifold and each of said plurality of vessels.

Preferably the assembly is disposable. The manifold to vessel connection is conveniently made with a flexible tubing suitable for use with a peristaltic pump.

A preferred embodiment of cell culture apparatus (utilising multiple roller bottles) utilises spring clips for supporting the roller bottles releasably within the rotor.

Preferably means is provided for tilting the axis of the rotor to cause fluid to run towards the dip tubes. The tilt mechanism is usually only employed when the rotor is stationary. Advantageously, means is provided for preventing accidental tilting, say in the manner of an interlock.

Preferably each channel of the pump is individually adjustable.

It is advantageous if each cell culture vessel can be removed from the rotor without having to disconnect the fluid connection thereto. This may be required to permit analysis of the culture (whilst in the bottle) using a microscope. This can be readily made possible by providing a sufficient length of tubing between the manifold and the vessel. When the apparatus is in use with the cell culture vessels located in the rotor the excess length of tubing is conveniently wrapped around a neck portion of the cell culture vessel. A clipping system is employed to hold the tube in place. Alternatively a separate tube storage means may be provided on the rotor.

It is preferred for each bottle to have the same length of vessel to manifold connection.

Another aspect of the invention provides a multichannel peristaltic pump comprising one or more of the following features, namely individual adjustment of the channels by way of a respective pump shoe and means for selectively opening and closing the channels. More particularly, the means for closing a selected channel serves to lift the pump shoe of that channel so that the action of the pump is suspended for that channel.

Drive to the rotor is from a drive motor via a belt and pulley system.

According to a yet further aspect of the invention there is provided a rotor drive system in which a flexible coupling is disposed in the drive train.

Preferably the flexible coupling has a high degree of torsional compliance and advantageously it is disposed between a drive motor and a pulley of a belt drive. It is also preferred to have a flywheel in the drive train and advantageously disposed between the flexible coupling and said pulley. The preferred drive train allows a stepping motor to be employed.

The various aspects of the present invention will now be described further hereinafter, by way of example only, with reference to the accompanying drawings, in which:BRIEF

BRIEF DESCRIPTION OF THE DRAWINGS

FIG. 5 is a cross section through one channel of a pump for use in the invention with the said channel set in the pumping mode, FIG. 6 is a cross section through one channel of the pump in FIG. 5 with the channel set in the clamped, or non-pumping mode, FIGS. 8 and 9 are perspective views showing the means by which excess tubing is stored.

MODES FOR CARRYING OUT THE INVENTION

Figure 1:
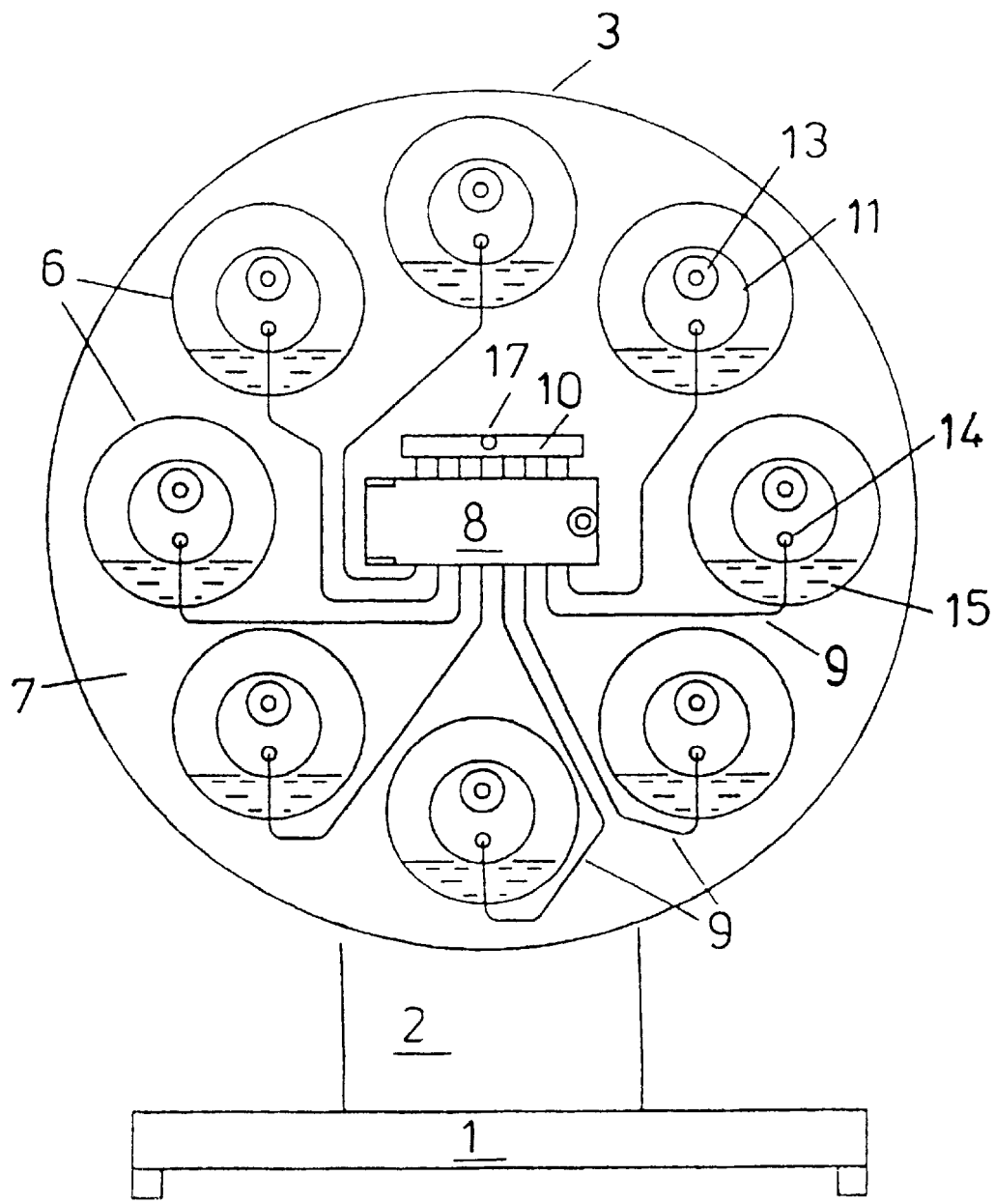
FIG. 1 is a front view of the apparatus according to one aspect of the present invention.
Figure 2:
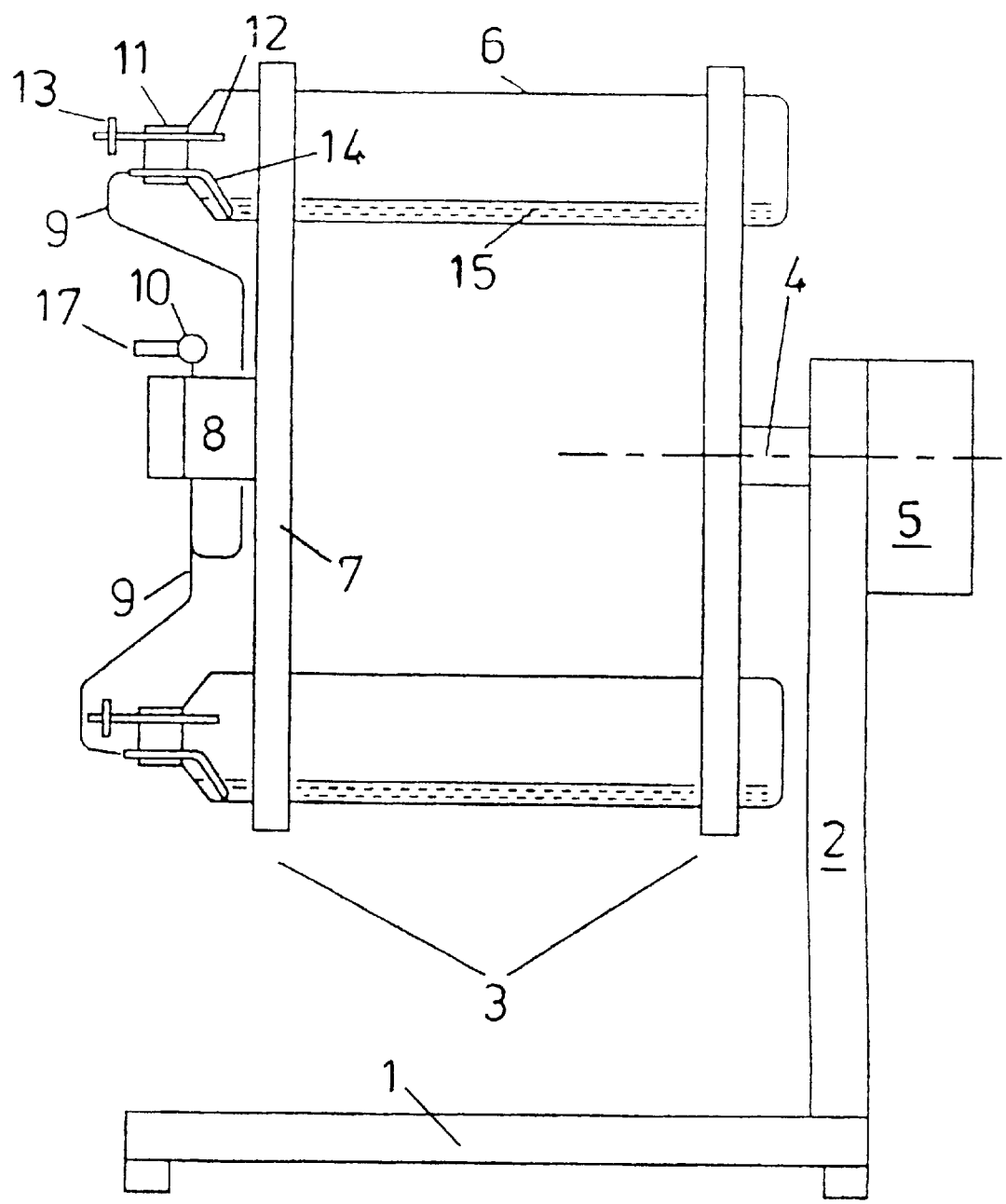
FIG. 2 is a sectional side view of the apparatus in FIG. 1.
Figure 3:
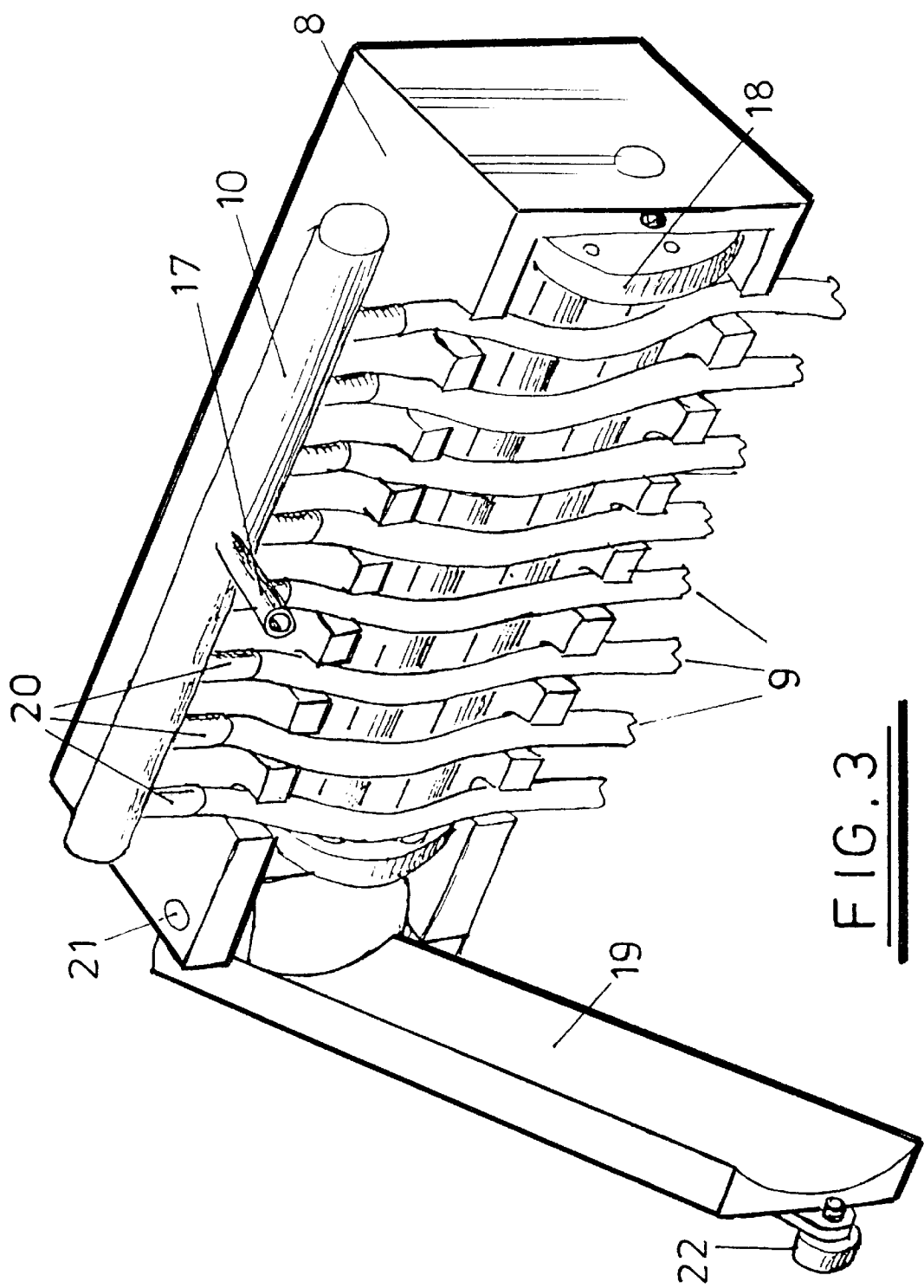
FIG. 3 is a perspective view of one embodiment of multi-channel pump and manifold assembly for use in the present invention.

Referring firstly to the drawings of FIGS. 1 to 3, the apparatus comprises a chassis 1 and rear rotor support 2 which supports a rotor 3 that is able to rotate about a horizontal shaft or axis 4. The rotor is driven by a motor and gearbox assembly 5 under the influence of a control system, not shown, such that its speed may be varied.

The rotor 3 releasably houses a plurality of roller bottles 6. The front rotor plate 7 provides mounting for a reversible multi-channel peristaltic pump 8, pump tubes 9 and manifold assembly 10. The roller bottles 6 are fitted with dip tube/vent cap assemblies 11. Air vents 12 communicate to atmosphere via microporous filters 13. The dip tubes 14 are extended downwards from the axis of the cap 11 on the interior of the bottle 6 so as to dip into the process fluid 15 when the rotor is in the upright position as shown.

The dip tubes 14 of the cap assemblies 11 are individually connected to the branches 20 of the manifold assembly 10 using flexible pump tubes 9 via the reversible multi-channel peristaltic pump 8. The pump tubes 9 are located against the pump rotor 18 by a pump shoe 19 that is pivoted about hinge 21 and is secured in the closed position by locking screw 22. The pump tubes 9 may be secured to the front rotor plate 7 by tube support clips, not shown, provided as required. The manifold assembly 10 is secured to the front rotor plate 7 by releasable means such that the dip tube/vent cap assemblies 11, pump tubes 9, and manifold assembly 10 may be removed for sterilisation whilst still interconnected.

A sealable external connection port 17 communicates with the manifold 10 such that the said manifold may be connected to an external reciever or vessel, not shown, for the purposes of injecting or extracting fluid. Metered quantities of process fluid may thus be transfered into or out of all of the bottles 6 simultaneously by stopping the rotor 3 in the upright position such that the dip tubes 14 are dipping into the culture medium 15, before making an aseptic connection to the connection port 17, and operating the pump 8 as required.

Provision may be made to tilt the rotor 3 on its axis by a few degrees so as to cause the fluid 15 to run towards the dip tube 14 end of the roller bottles 6, thus minimizing the residue left in the bottle after emptying.

Electrical power for operation of the pump 8 is provided by slip rings, not shown, operating between the chassis 1 and the rotor 3. The pump 8 may be controlled by a presettable counter, not shown, that stops the pump 8 after a preset number of revolutions of the pump rotor 18, in this manner, an automatically metered quantity of fluid may be transferred into or out of the bottles 6 as required.

The peristaltic pump 8 may be mounted releasably to the front rotor plate 7 such that a single pump may be used to process a number of rotors 3 sequentially, thus eliminating the cost of providing each rotor 3 with its own pump 8. In such an embodiment, clamping means, not shown must be provided on each rotor 3 to occlude the individual pump tubes 9 and thus prevent siphoning of fluid between bottles when the pump 8 is removed.

The connection port 17 may be connected to a non-rotating system, not shown, by a flexible umbilical tube, not shown, that allows limited rotation of the rotor 3, yet still allows the transfer of fluid. Excessive twisting of the umbilical is prevented by providing automatic means to periodically reverse the direction of rotation of the rotor 3.

The connection port 17 may be connected to a non-rotating system, not shown, via a rotary coupling, thus allowing the rotor 3 to rotate, whilst also providing for the transfer of fluid. In such an embodiment, the rotation of the rotor 3 may be unidirectional.

The rotation of the rotor 3 and the operation of the pump 8 may be under the influence of an automatic timing and control system, not shown, that facilitates the automatic transfer of fluids to/from the aforementioned non-rotating system.

The apparatus may be equipped with a removable insulated hood, or cover, and provided with an electrically operated air heater and temperature control system, not shown. The arrangement being such that the apparatus may automatically regulate the temperature of the bottles 6, without the need to place the apparatus within an incubator or temperature controlled environment.

Means may be provided to disable selected channels of the multi-channel pump 8, by lifting a corresponding section of the pump shoe 19 clear of the pump rotor 18, and occluding the corresponding pump tube by clamping means, not shown. The arrangement being such that fluid may be pumped into or out of selected bottles within the apparatus.

Figure 4:
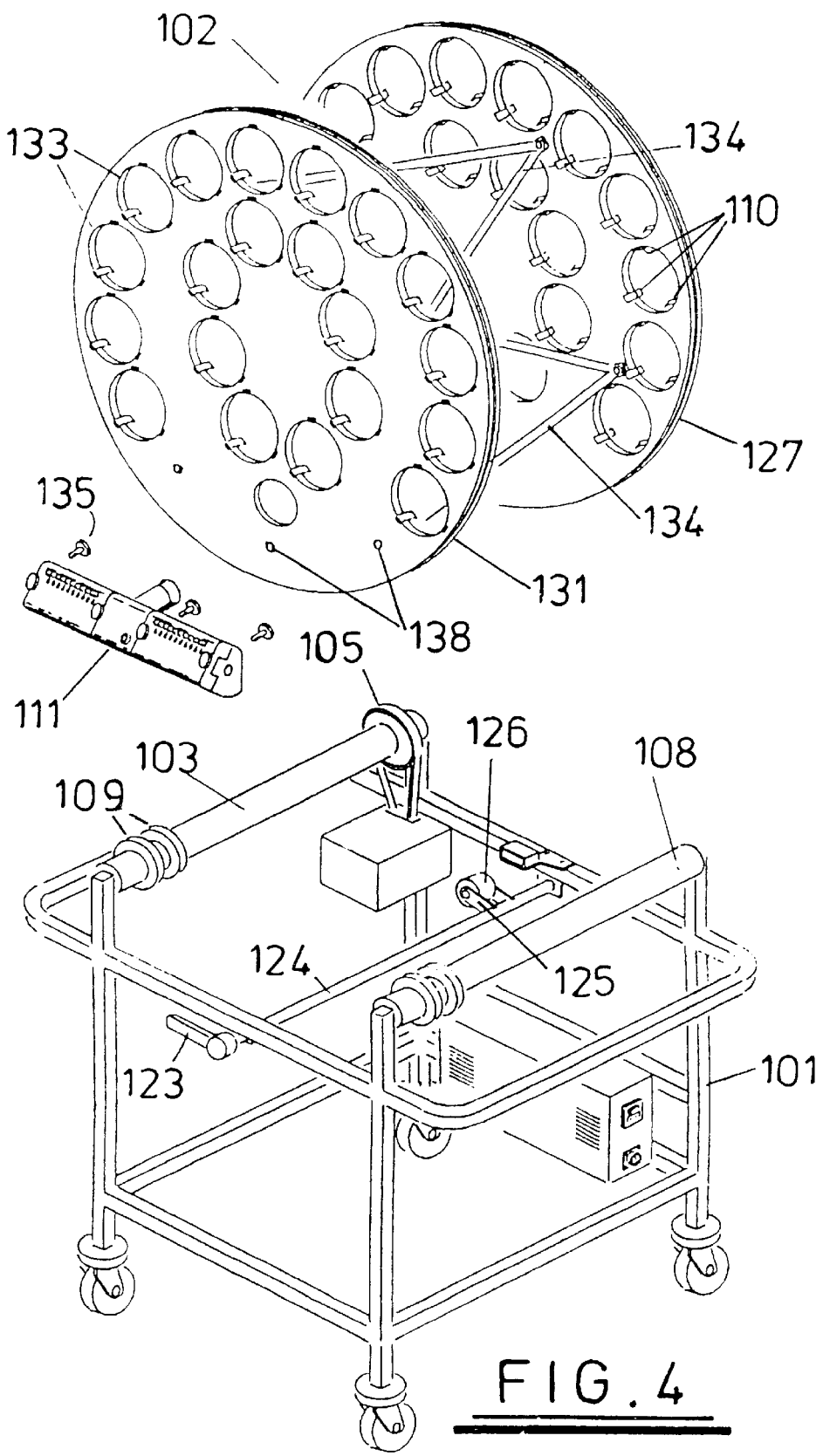
FIG. 4 is an exploded perspective view of apparatus embodying the various aspects of the present invention.

Referring now to FIG. 4, a preferred embodiment of apparatus comprises a wheeled chassis 101, supporting a demountable rotor 102, by means of a drive roller 103 and a support roller 108, such that rotation of the drive roller 103 results in rotation of the rotor. A drive motor is located below the cover 132 and turns the drive roller 103 via a belt and pulley system 105. Both rollers 103 and 108 are equipped with collars 109, that constrain the rotor 102 from axial movement by locating either side of the front rotor plate 131.

The rotor 102 releasably houses a multiplicity of roller bottles, not shown, by means of spring clips 110 which grip the bottles radially within the holes 133 in the rotor plates, there being three spring clips 110 in each hole 133, such that both ends of the bottles are fully supported when inserted through the holes. The front 131 and rear 127 rotor plates are rigidly held together by means of triangulated bracing struts 134, the ends of the said struts being releasably located to the rotor plates such that the rotor assembly 102 may be dismantled for transport or storage.

A rotor tilt lever 123 acts via shaft 124 upon a crank arm 125 and roller 126, the arrangement of the parts is such that by turning the tilt lever 123 clockwise, roller 126 acts upwards upon the rim of the rear rotor disc 127, and lifts the rear of the rotor. Tilting the rotor in this manner ensures ensures complete emptying of the bottles when pumping out fluid.

The rotation of shaft 124 is constrained by-stops, not shown, in both the tilted and lowered positions. When the rotor tilt handle 123 is in the lowered position, a switch is actuated. The control system, not shown, is interlocked to prevent rotation of the rotor unless the rotor 102 is lowered to the horizontal.

The control system may also prevent fluid being pumped out unless the rotor 102 is tilted.

A multi-channel peristaltic dosing pump 111 is releasably mounted upon the rotor 102, by means of retaining screws 135 and location holes 138.

Referring to FIG. 5, each channel of the pump is equipped with a movable section of pump shoe 112, and tube clamp 113. The movable pump shoe 112 acts about a hinge 114, which in this example is formed by flexing a narrow portion of the shoe 112 material. The shoe 112 is urged onto the pump rollers 115 by a spring 116. The minimum gap between the rollers 115 and the inner surface of the pump shoe 112 is set by an adjusting screw 117 acting against the pump cover 118. There is one such adjusting screw for each channel. The tube clamp 113 is shown in the retracted position, rotation of the pump will thus cause fluid to be displaced through the tube 119.

Referring to FIG. 6, the tube clamp 113 may be extended by actuation of the clamping screw 120, thus occluding the tube 119 between the cap 123 and a block 121 that is fixed to the pump body 122. The action of extending the clamp 113 also has the effect of lifting the pump shoe 112 away from the rollers 115, compressing spring 116. This prevents the pump tube 119 from being damaged by excessive pressure build up in the clamped channel when the pump is operated to process bottles connected to other unclamped channels. By this means it is possible to selectively transfer fluid into or out of, any, or all of the roller bottles as desired.

Figure 7:
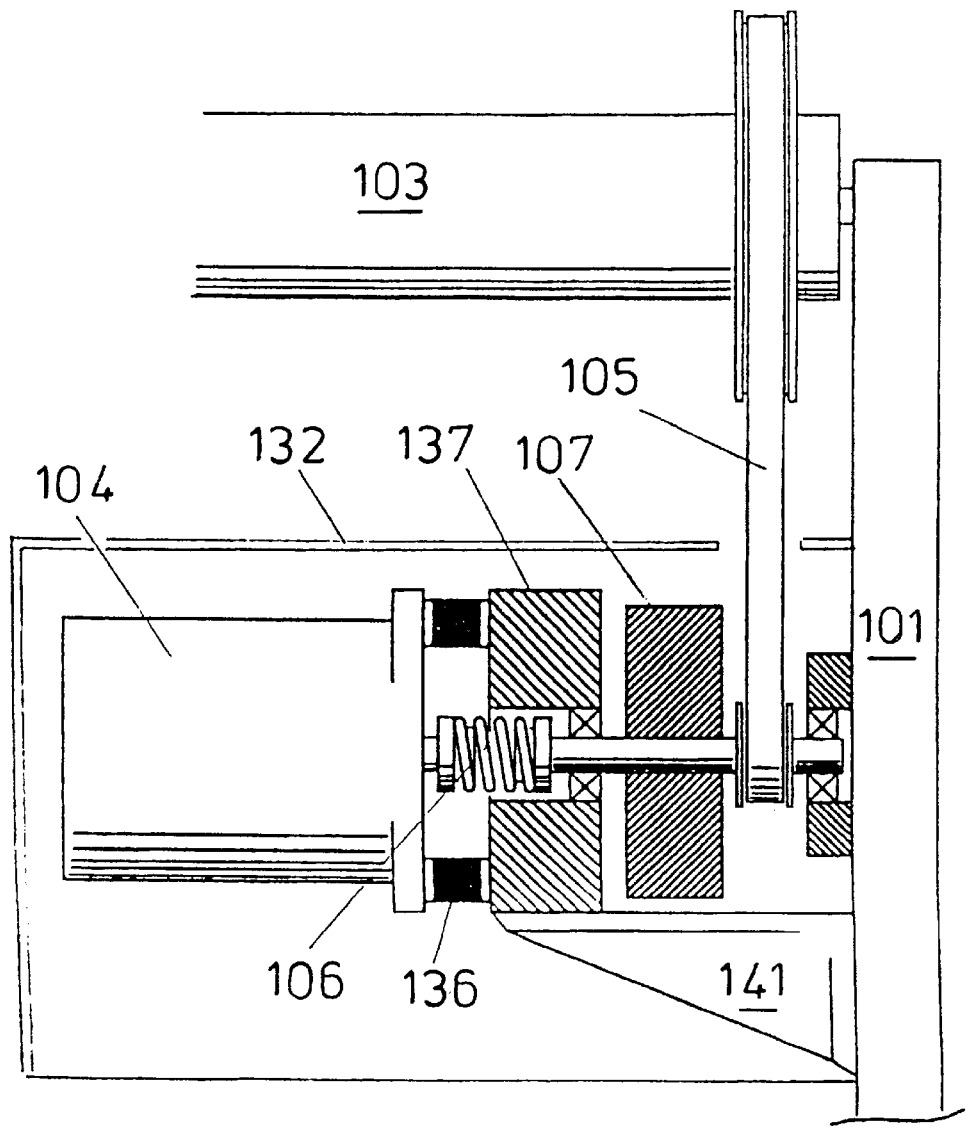
FIG. 7 is a cross section through a rotor drive system.

Referring to FIG. 7, rotation of the rotor 102, is facilitated by means of drive motor 104, acting upon drive rollers 103 via a belt and pulley system 105.

A flexible coupling 106, in this embodiment a spring drive, and a flywheel 107 may be interposed between the motor 104 and the belt and pulley system 105, to isolate the drive rollers 103 from torsional vibrations of the motor 104 and ensure smooth rotation of the rotor. The motor 104 itself is located in resilient mountings 136, to prevent vibration being transmitted into the chassis 101. The motor mountings 136 are secured to a ballast weight 137 that in in turn mounted upon the chassis 101 by a bracket 141. The ballast weight 137 has the effect of further reducing the magnitude of any residual vibration in the chassis 101.

By this arrangement, it is possible to utilise a stepping motor to drive the rotor without compromising cell attachment and growth as a result of excessive vibration.

The use of a stepper motor in this application has advantages in that a very wide rotor speed range can be accomodated, typically from 0.1 rpm for cell attachment, up to typically 15 rpm so as to allow rinsing or washing of the cell sheet. The use of DC servo motors is also possible in this application, but analogue systems of this type frequently have difficulty in providing accurate and stable rotational speed over such a wide speed range.

In order to assure accurate dosing of small quantities of fluid, all the pump tubes 119 are the same length, the length being sufficient to allow the bottles to be inserted into or withdrawn from the rotor 102 while the tubes 119 are loaded into the pump 111. Referring to FIG. 8. A bottle 139 is shown positioned within its mounting hole 133. The spring retaining clips 110 are not shown for clarity. Since, in the embodiment shown, some bottles are much nearer to the pump than others, means are provided to accomodate excess tube length. The bottle caps, or the bottles themselves are provided with tube storage means, in this example, a tube location disc 128, equipped with a number of tube retaining slots 129, about its periphery. Excess tubing is wound upon the said tube storage means, or in this example, around the neck 130 of the bottle 139, as it protrudes from the front rotor plate 131. When winding the tube around the bottle neck 130, the tube 119 is twisted in the same direction as it is wound so as to cancel the inherent twist produced by winding, and thus prevent kinking of the final section of tube. In FIG. 8, the winding direction is shown as being anti-clockwise as indicated by arrow 'A'. The tube is therefore twisted one turn anti-clockwise for each turn of tubing that is stored around the bottle neck 130. The direction of twist is indicated by arrow 'B'.

The final loose section of tubing is then secured into one of the retaining slots 129 as shown in FIG. 9.

Clips 140 are provided as required on the front rotor plate 131 to allow storage of the lengths of tubing 119 connecting the individual bottles to the multi-channel peristaltic pump 11, not shown.

Figure 10:
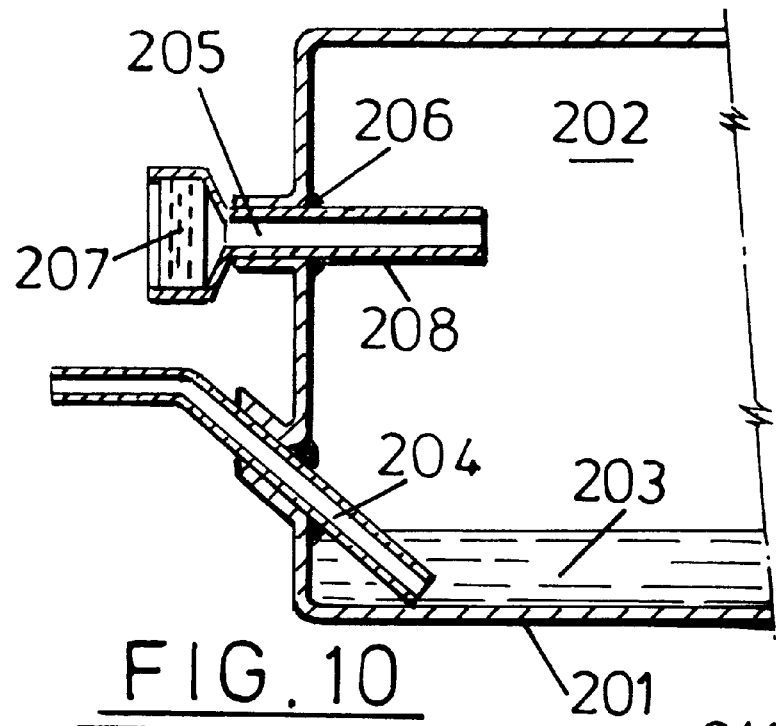
FIG. 10 shows a longitudinal cross section through a cell culture vessel.

Referring to FIG. 10, the cell culture vessel/roller bottle according to the invention comprises a substantially cylindrical vessel 201, equipped with dip tube 204 that allows the vessel to be filled or emptied by a connecting tube, not shown, that communicates with a multi-channel peristaltic pump, likewise not shown. In the embodiment shown, the dip tube 204 is a separate item bonded into the vessel 201 so as to form a seal, but it may be moulded integrally as an extension of the vessel wall 101.

As fluid 203 is displaced into or out of the vessel, the volume of air in the head space 102 changes. Pressure equalization with the atmosphere is provided by a vent 205, that communicates with the head space 102 via a microporous filter element 207 that prevents the entry of contaminants or foreign organisms. A fluid trap is provided by a constructed extension of the filter housing 208 that extends into the body of the vessel 202 and prevents the fluid 203 from splashing into the filter 207 if the vessel is moved or shaken.

In the embodiment shown, the filter housing 208 is bonded into the vessel 201 by an adhesive/sealant 206, although the filter housing may also be moulded integrally with the vessel 201.

Figure 11:
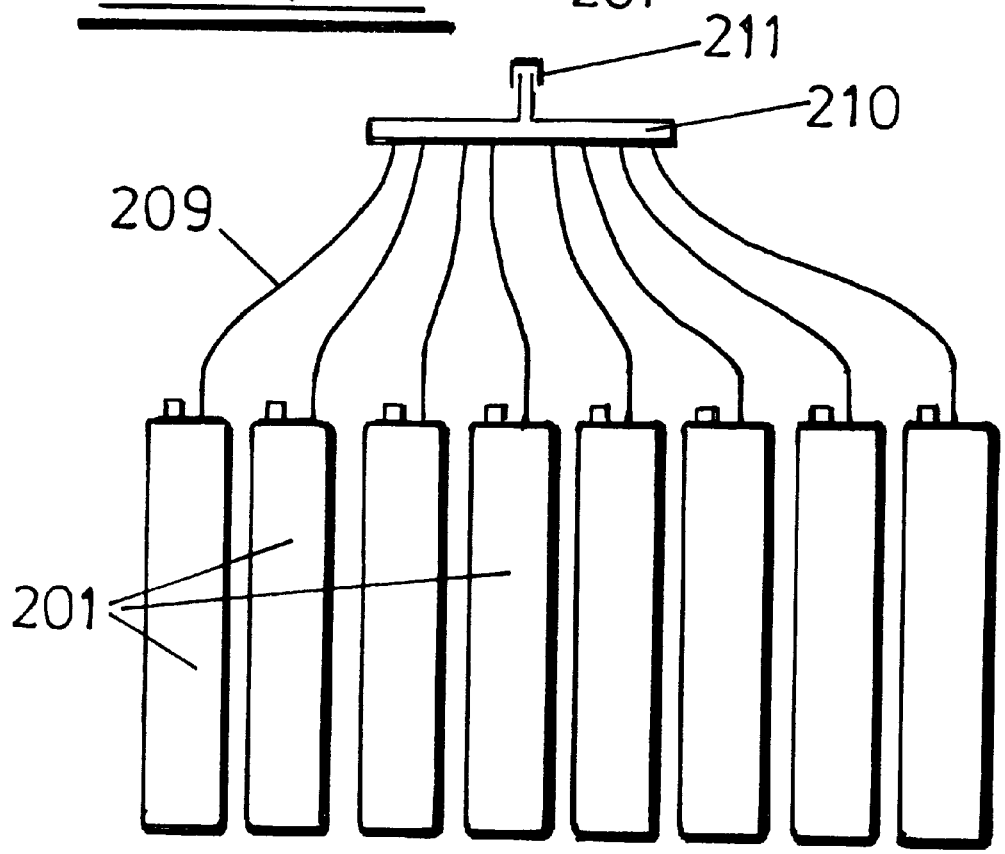
FIG. 11 shows a multiplicity of cell culture vessels connected into a cell culture vessel assembly, complete with interconnecting pump tubes, manifold and external connection port.

Referring to FIG. 11, a multiplicity of bottles 201 may be connected into a re-usable or disposable assembly that includes tubes 209, manifold 210, and sealable external connection 211. The said assembly may then be sterilised whilst interconnected, by heat, chemically, or by irradiation, thus eliminating the need to connect the tubes 209 to the bottles 201 under aseptic conditions whilst setting up the apparatus. This method of working substantially reduces the likelyhood of contamination.

It will be understood that bottles 201 can be used in place of the bottles 6 and/or 139 referred to earlier.

What is claimed is:

1. A cell culture apparatus, comprising:

a supporting frame, a rotor releasably housing a plurality of vessels, the rotor being mounted for rotation about a substantially horizontal axis and supported by the frame; and means for effecting rotation of the rotor at a controlled speed, at least one reversible multi-channel pump, mounted on said rotor for rotation therewith, a manifold including at least one sealable external connection and a plurality of connections each in fluid communication with an individual channel of the pump, a vent coupled to each vessel and in fluid communication with the atmosphere, a dip tube coupled to each vessel, the dip tube of each vessel being individually connected to one channel of the pump, the dip tube being fixed with respect to the vessel and positioned to permit extraction of fluid when the vessel is stopped in a specific orientation, wherein the rotor, vessels, pump, manifold and the connections to the vessels are rotatable about the horizontal axis, and fluid may be injected into or extracted from the vessels simultaneously via said one external connection under the influence of the pump.

2. The cell culture apparatus as recited in claim 1, wherein the vent is a microporous filter that provides venting of the vessels by means of a multi-way vent manifold and corresponding plurality of vent manifold to vessel vent connections.

3. The cell culture apparatus as recited in claim 1, wherein the pump is a peristaltic type pump and is releasably located on the rotor, such that a single pump may service a plurality of rotors sequentially.

4. The cell culture apparatus as recited in claim 3, further comprising a closure means operable between the manifold and the vessels, such that operation of the closure means prevents siphoning of fluid between the vessels when the pump is removed from the rotor.

5. The cell culture apparatus as recited in claim 4, wherein the rotor is releasably located upon the supporting frame.

6. The cell culture apparatus as recited in claim 1, wherein the vessels, vents, vessel to manifold connections, manifold, and a manifold external connection is releasably located on the rotor such that the vessels, vents, connections, manifold and manifold external connection may be sterilized while interconnected before being located onto the rotor.

7. The cell culture apparatus as recited in 6, further comprising a closure means operable between the manifold and the vessels, such that operation of the closure means prevents siphoning of fluid between the vessels when the pump is removed from the rotor.

* * * * *